(12) United States Patent
Eggen et al.

(10) Patent No.: US 7,435,791 B2
(45) Date of Patent: *Oct. 14, 2008

(54) PROCESS FOR RAPID SOLUTION SYNTHESIS OF PEPTIDES

(75) Inventors: Ivo Franci Eggen, Oss (NL); Paulus Bernardus Wilhelmus Ten Kortenaar, Oss (NL); Cornelis Albert Gruson Haasnoot, Oss (NL)

(73) Assignee: N.V. Organon, Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/693,802

(22) Filed: Oct. 23, 2003

(65) Prior Publication Data

US 2004/0087768 A1 May 6, 2004

Related U.S. Application Data

(62) Division of application No. 10/199,805, filed on Jul. 19, 2002, now abandoned.

(30) Foreign Application Priority Data

Jul. 19, 2001 (EP) .................................. 01202753

(51) Int. Cl.
*C07K 1/02* (2006.01)

(52) U.S. Cl. ........................................ 530/338; 506/27

(58) Field of Classification Search ........................ None
See application file for complete search history.

(56) References Cited

U.S. PATENT DOCUMENTS

| | | | |
|---|---|---|---|
| 5,101,059 A | 3/1992 | Carpino et al. | |
| 5,221,754 A | 6/1993 | Carpino et al. | |
| 5,510,491 A | 4/1996 | Carpino et al. | |
| 5,516,639 A | 5/1996 | Tindall et al. | |
| 5,652,336 A | 7/1997 | Fife et al. | 530/342 |
| 5,698,676 A | 12/1997 | Dhaon | 530/334 |
| 5,877,278 A | 3/1999 | Zuckermann et al. | 530/334 |
| 6,001,966 A | 12/1999 | Pieken et al. | 530/338 |
| 6,121,488 A | 9/2000 | Nikam | |
| 6,204,361 B1 | 3/2001 | Carpino et al. | |
| 6,277,958 B1 | 8/2001 | Aimoto | |
| 6,310,180 B1 | 10/2001 | Tam | |
| 6,506,701 B1 | 1/2003 | Bolton et al. | 502/20 |
| 6,864,357 B2 * | 3/2005 | Eggen et al. | 530/333 |
| 2001/0025025 A1 | 9/2001 | Viskov | 514/9 |
| 2002/0127219 A1 | 9/2002 | Okkels et al. | |
| 2003/0017991 A1 | 1/2003 | Yan et al. | |
| 2004/0082760 A1 * | 4/2004 | Eggen et al. | 530/333 |

FOREIGN PATENT DOCUMENTS

WO 00 71569 11/2000

WO WO 00/71569 * 11/2000

OTHER PUBLICATIONS

Carpino, et al. The 1,1-Doxobenzo[b]thiophene-2-ylmethyloxycarbonyl (Bsmoc) Amino-Protecting Group J. Org. Chem. 1999, 64, 4324-4338.*

Solomons, T. W. G. Organic Chemistry Fifth Edition. New York: John Wiley and Sons. 1992, p. 94, Table 3.1.*

Houghten, R.A.; Pinilla, C.; Blondelle, S.E.; Appel, J.R.; Dooley, C.T.; Cuervo, J.H. "Generation and use of synthetic peptide combinatorial libraries for basic research and drug discovery" Nature 1991, 354, 84-86.*

CRC Handbook of Chemistry and Physics, ed. DA Lide, 85th edn., CRC Press, Cleveland, OH, 2004-2005, web page 1.*

STN Express, Registry No. 141-43-5, chemical properties Isiting including pka values, taken Jan. 20, 2007, p. 1.*

Carpino et al: "The 1,1-Dioxobenzo[b] thiophene-2-ylmethyloxycarboyl (Bsmoc) Amino-Protecting Group"; J. Org. Chem. 1999, vol. 64 pp. 4324-4338.

Bernard et al: "Peptide Synthesis by Sappho Technology"; Industrial Chemistry Library, 1996, pp. 405-415.

Sugawara et al: "A solution-phase synthesis of Fragment Peptide Derivatives Using an Automated Synthesis Apparatus"; Peptide Chemistry, 1996, vol. 33, pp. 57-60.

Nozaki et al: "Rapid Peptide Synthesis in Liquid Phase . . . "; Bull. Chem. Soc. JP., 1982, 55(7), pp. 2165-2168.

(Continued)

*Primary Examiner*—Jon D Epperson
(74) *Attorney, Agent, or Firm*—Susan Hess

(57) ABSTRACT

The present invention relates to a process for rapid solution synthesis of a peptide, the process comprising repetitive cycles of steps (a)-(d):

(a) a coupling step, using an excess of an activated carboxylic component to acylate an amino component, (b) a quenching step in which a scavenger is used to remove residual activated carboxylic functions, wherein the scavenger may also be used for deprotection of the growing peptide, (c) one or more aqueous extractions and optionally, (d) a separate deprotection step, followed by one or more aqueous extractions, characterised in that the process comprises at least one step (b), referred to as step (b'), in which an amine or a thiol comprising a free anion or a latent anion is used as a scavenger of residual activated carboxylic functions.

During the process of this invention the growing peptide need not be isolated until the final peptide sequence has been obtained.

This highly efficient process is useful for the production of oligo- and polypeptides of high purity.

37 Claims, No Drawings

OTHER PUBLICATIONS

Cheng et al: "Liquid phase parallel synthesis . . . "; Tetrahedron Letters 40, 1999, pp. 8975-8978.

Wallace et al: "Microsystem technology: a powerful tool for biomolecular studies . . . "; Biomethods, 1999, 10, pp. 225-240.

Gravert et al: "Soluble polyethylene glycol supports for . . . "; Combinatorial Chemistry and Drug Discovery, 1997, 22 (10), pp. 1147-1150.

Gaylo L M et al: "Ion-Exchange Resins for Solution Phase Parallel Synthesis of Chemical Libraries"; Tetrahedron Letters, Elsevier Science Publishers, Amsterdam, NL; vol. 38, No. 4, Jan. 27, 1997, pp. 513-516.

Suto M J et al: "Solution-Phase Parallel Synthesis Using Ion-Exchange Resins" Tetrahedron, Elsevier Science Publishers, Amsterdam, NL, vol. 54, No. 16, Apr. 16, 1998, pp. 4141-4150.

Mehta A et al: "Improved efficiency and selectivity in peptide synthesis use of triethylsilane as a carbocation scavenger in deprotection of tert butyl esters and tert butoxycarbonyl-protected sites", Tetrahedron Letters, vol. 33, No. 37, 1992, pp. 5441-5444.

Mutter et al. "The Liquid-Phase Method for Peptide Synthesis"; The Peptides, vol. 2, pp. 285-332, (1979).

Pinilla et al. "Synthetic peptide combinatorial libraries (SPCLs) : Identification of the antigenic determinant of b-endorphin recognized by monoclonal antibody 3E7". Gene; vol. 128, pp. 71-76 (1993).

Kisfaludy et al. "A novel and rapid peptide synthesis". Tetrahedron Letters, vol. 15, pp. 1785-1786 (1974).

European Search Report for Application No. EP 01 20 2753 dated Jun. 28, 2002.

Derwent abstract No. 0000135378 abstracting SU 215 227.

Fukuyama, T. et al, "2,4-Dinitrobenzenesulfonamides: A Simple and Practical Method for the Preparation of a Variety of Secondary Amines and Diamines," Tetrahedron Letters, vol. 38, No. 33 (1997) pp. 5831-5834.

Kisfaludy, L. et al., "A Novel and Rapid Peptide Synthesis," Tetrahedron Letters, No. 19 (1974) pp. 1785-1786.

Kunz, H. et al, "Der Allyloxycarbonyl(Aloc)-Rest—die Verwandlung einer untauglichen in eine wertvolle Aminoschutzgruppe für die Peptidsynthese," Angew. Chem., vol. 96, No. 6 (1984) pp. 426-427.

English language version of Kunz, H. et al., "The Allyloxycarbonyl (Aloc) Moiety—Conversion of an Unsuitable into a Valuable Amino Protecting Group for Peptide Synthesis," Angew. Chem. Int. Ed. Engl., vol. 23, No. 6 (1984) pp. 436-437.

Karlström, A. et al., "A New Protecting Group for Aspartic Acid that Minimizes Piperidine-Catalyzed Aspartimide Formation In Fmoc Soliid Phase Peptide Synthesis," Tetrahedron Letters, vol. 37, No. 24 (1996) pp. 4243-4246.

Yue, C. et al., "2-Phenyl Isopropyl Esters as Carboxyl Terminus Protecting Groups in the Fast Synthesis of Peptide Fragments," Tetrahedron Letters, vol. 34, No. 2 (1993) pp. 323-326.

Athanassopoulos, P. et al., "Application of 2-Chlorotrityl Chloride in Convergent Peptide Synthesis," Tetrahedron Letters, vol. 36, No. 31 (1995) pp. 5645-5648.

Mergler, M. et al., "Systematic Investigation of the Aspartimide Problem," Proceedings of the Second International and the Seventeenth American Peptide Symposium (Jun. 9-14, 2001) pp. 63-64 and title pages (2 sheets).

Carpino, L. A. et al, "Novel Carboxylic Acid and Carboxamide Protective Groups Based on the Exceptional Stabilization of the Cyclopropylmethyl Cation," J. Org. Chem., vol. 60 (1995) pp. 7718-7719.

Al-Obeidi, F. et al., "Synthesis of β- and γ-fluorenylmethyl esters of respectively $N^\alpha$-Boc-L-aspartic acid and $N^\alpha$-Boc-L-glutamic acid," Int. J. Peptide Protein Res., vol. 35 (1990), pp. 215-218.

Kunz, H. et al., "Allyl ester as temporary protecting group for the β-carboxy function of aspartic acid," Int. J. Peptide Protein Res., vol. 26 (1985) pp. 493-497.

Sieber, P. with English Summary, "264. Der 2-Trimethylsilyläthyl-Rest als selektiv abspaltbare Carboxy-Schutzgruppe," Helvetica Chimica Acta, vol. 60 , No. 8 (1977) pp. 2711-2716.

Chan, W. C. et al., "A Novel 4-Aminobenzyl Ester-based Carboxy-protecting Group for Synthesis of Atypical Peptides by Fmoc-Bu$^t$ Solid-phase Chemistry," J. Chem. Soc., Chem. Commun., (1995) pp. 2209-2210.

Li, P. et al., "Highly efficient synthesis of peptides by rational utilization of novel coupling reagents," Chinese Journal of Chemistry, vol. 18, No. 4 (2000) pp. 456-466.

Franzén, H. et al., "Synthesis, Properties, and Use of $N^{in}$-Boc-tryptophan Derivatives," J. Chem. Soc., Chem. Commun. (1984) pp. 1699-1700.

Sieber, P. et al., "Protection of Carboxamide Functions by the Trityl Residue. Application to Peptide Synthesis," Tetrahedron Letters, vol. 32, No. 6 (1991) pp. 739-742.

Sieber, P. et al., "Protection of Histidine in Peptide Synthesis: A Reassessment of the Trityl Group," Tetrahedron Letters, vol. 28, No. 48 (1987) pp. 6031-6034.

Ramage, R. et al., "$N_G$-2,2,5,7,8-Pentamethylchroman-6-Sulphonyl-L-Arginine: A New Acid Labile Derivative for Peptide Synthesis," Tetrahedron Letters, vol. 28, No. 20 (1987) pp. 2287-2290.

Carpino, L. A. et al., "The 2,2,4,6,7-Pentamethyldihydrobenzofuran-5-sulfonyl Group (Pbf) as Arginine Side Chain Protectant," Tetrahedron Letters, vol. 34, No. 49 (1993) pp. 7829-7832.

Eggen, I. F. et al., "A novel method for repetitive peptide synthesis in solution with isolation of intermediates," Journal of Peptide Science, vol. 11 (2005) pp. 633-641.

Eggen, I. F. et al., "DioRaSSP: Diosynth Rapid Solution Synthesis of Peptides," Organic Process Research & Development, vol. 9 (2005) pp. 98-101.

Eggen, I. F., "DioRaSSP®: Diosynth Rapid Solution Synthesis of Peptides," Poster (2004).

Eggen, I. F., "Extending the potentials of the DioRaSSP® method," Power Point Presentation (2004).

Ludt, R. E. et al., "A Comparison of the Synthetic Utility of n-Butyllithium and Lithium Diisopropylamide in the Metalations of N,N-Dialkyltoluamides," J. Org. Chem., vol. 38, No. 9 (1973) pp. 1668-1674.

Tsuboi, S. et al., "Stereoselective Transformation of 2,4-Alkadienoic Esters to the 3,5-Dienoic Isomers with Lithium Diisopropylamide (LDA)," Chemistry Letters (9) (1984) pp. 1541-1542.

Dragovich, P. S. et al., "Formal Stereoselective Synthesis of Hydroxyethylene Dipeptide Isosteres Utilizing Pseudoephedrine Amides," J. Org. Chem., vol. 62, No. 22 (1997) pp. 7872-7876.

Mallet, M. et al. with English Abstract, "Reaction De La Bromo-3 Pyridine Avec Le Diisopropylamidure De Lithium. Mecanismes de Metallation Et De Migration D'Halogene. Regioselective De L'Addition Polaire Sur La Pyridyne-3,4," Tetrahedron, vol. 38, No. 20 (1982) pp. 3035-3042.

Balamraju, Y. et al., "Mixed Aggregates of Lithium Tetramethylpiperidide with Butyllithium: Stereoselectivity of Ketone Enolization," Tetrahedron, vol. 54, No. 26 (1998) pp. 7357-7366.

Kazmaier, U. et al., "Application of the chelate enolate Claisen rearrangement to the modification of dipeptides," Chemical Communications, Cambridge (22) (1998) pp. 2535-2536.

Carpino, L. A. et al., "Piperazino-Functionalized Silica Gel as a Deblocking-Scavenging Agent for the 9-Fluorenylmethyloxycarbonyl Amino-Protecting Group," J. Org. Chem., vol. 48 (1983) pp. 666-669.

Carpino, L. A. et al., "Polystyrene-Based Deblocking-Scavenging Agents for the 9-Fluorenylmethyloxycarbonyl Amino-Protecting Group," J. Org. Chem., No. 48 (1983) pp. 661-665.

Carpino, L. A. et al., "Tris(2-aminoethyl)amine as a Substitute for 4-(Aminomethyl)piperidine in the FMOC/Polyamine Approach to Rapid Peptide Synthesis," J. Org. Chem., vol. 55 (1990) pp. 1673-1675.

Russian Search Report dated Jan. 23, 2003.

Israelian office action dated Oct. 16, 2002.

Domb, A. J. et al., "Chemical Interactions Between Drugs Containing Reactive Amines with Hydrolyzable Insoluble Biopolymers in Aqueous Solutions," Pharmaceutical Research, vol. 11, No. 6 (1994) pp. 865-868.

Supporting Information for Carpino et al., The 1,1-Dioxobenzo[b]thiophene-2-ylmethyloxycarbonyl (Bsmoc) Amino- Protecting Group. Jun. 11, 1999, J. Org. Chem., vol. 64, No. 12, pp. 4324-4338. Supporting Info. pp. 1-133.

Houghten, R.A. et al, "Generation and use of the synthetic peptide combinatorial libraries for basic research and drug discovery," Letters to Nature, vol. 354 (1991) pp. 84-86.

Eggen et al., "Rapid solution-phase synthesis of a 20-mer peptide according to the DioRaSSP method," *Supplement to Chimica Oggi/Chemistry Today 23* (2005) 21-24.

* cited by examiner

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(4)
<223> OTHER INFORMATION: Description of Artificial Sequence:
      Synthetic peptide, Boc at N- and tBu-ester at C-terminus;
      tBu-ester at Asp side chain; tBu-ether at Ser side-chain

<400> SEQUENCE: 1

Gly Phe Asp Ser
1

<210> SEQ ID NO 2
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(8)
<223> OTHER INFORMATION: Description of Artificial Sequence:
      Synthetic peptide, tBu-ether at Ser and Tyr side-chains;
      Leu at positin 5 is D-Leu; tBu-ester at C-terminus
<220> FEATURE:
<221> NAME/KEY: MISC_FEATURE
<222> LOCATION: (7)..(7)
<223> OTHER INFORMATION: Xaa at position 7 is Orn with Boc on Orn
      side-chain

<400> SEQUENCE: 2

His Trp Ser Tyr Leu Leu Xaa Pro
1               5

PROCESS FOR RAPID SOLUTION SYNTHESIS OF PEPTIDES

RELATED APPLICATION

This application is a divisional of patent application U.S. Ser. No. 10/199,805, filed Jul. 19, 2002, now abandoned.

FIELD OF THE INVENTION

The invention relates to a new and versatile process for rapid solution synthesis of peptides, wherein the growing peptide need not be isolated before the assembly of the desired sequence is completed.

BACKGROUND OF THE INVENTION

Peptides are synthesized either on a solid support or in solution. In both approaches coupling and deprotection steps repetitively alternate and may be separated by intermittent purifications. In the solid phase approach, a sequence is assembled completely while attached to a solid support before it is eventually cleaved from said support. Removal of excess reagents and by-products takes place by filtration. Solid phase synthesis clearly has advantages: it is more or less generally applicable and easy to automate. However, it has also some serious drawbacks. For example, reactions are diffusion-controlled and are usually rather slow under the applied heterogeneous conditions: in order to avoid deletion sequences relatively large excesses of reagents are needed. In addition, all reactive side chains of the growing peptide must be protected: since no intermittent purifications take place, side reactions due to the presence of unprotected side chains may lead to impurities in the final product. The solid phase approach is difficult to scale up and it is costly in terms of reagents and materials.

The classical solution phase approach, on the other hand, is easier to scale up and is less expensive in terms of reagents and materials. Fully protected amino acids are usually not needed, since by-products resulting from side reactions of unprotected side chains may be removed by intermittent purifications. However, the solution phase approach requires sequence-specific protocols and the production of a complete sequence is very time-consuming.

Because of the drawbacks of these approaches there is a need for a process which combines the advantages of both these classical methods, in particular for large scale syntheses of peptides. A new process should be rapid, easy to scale up and generally applicable.

In solution phase synthesis, a slight excess of an activated carboxylic component is preferably used in each coupling step to ensure quantitative coupling to an amino component; thus the occurrence of deletion sequences in the final product can be avoided. It is usually assumed that the residual activated carboxylic component is destroyed and removed during the intermittent aqueous work-up. Insertion peptide sequences, however, are often encountered as impurities of the final peptide due to incomplete removal of residual (activated) carboxylic component after a coupling step, which subsequently has coupled following deprotection. In order to avoid the occurrence of said side reactions a scavenging step may be introduced directly after the coupling step to scavenge (inactivate) the residual activated carboxylic functions. Amines are usually applied as scavengers. The use of polyamines as scavengers leads to scavenged compounds which may be actively extracted into a—preferably acidic— aqueous phase, depending on their polarity [e.g. Kisfaludy, L. et al. (1974) *Tetrahedron Lett.* 19, 1785-1786]. This extraction is usually performed before the deprotection step to avoid loss of the growing peptide into the aqueous phase. However, this procedure has in numerous cases been found to result in incomplete intermittent purification due to the hydrophobicity of the scavenged compound: the intrinsic hydrophobicity of the amino acyl part of the carboxylic component is enhanced by the still present amino-protecting group. Aqueous extraction is thus not completely effective.

Recently, Carpino, L. A. et al. [(1999) *J. Org. Chem.* 64, 4324-4338] reported an improvement of the scavenging method. In addition to the use of a polyamine as a scavenger the amino-protecting group 1,1-dioxobenzo[b]thiophene-2-ylmethoxycarbonyl (Bsmoc) was applied in the process. The Bsmoc function has very high lability towards base. As a result thereof, residual activated carboxylic functions are scavenged and Bsmoc functions are removed in one and the same step using a polyamine. The use of the Bsmoc function has been described as a significant improvement for the production of (oligo)peptides using rapid continuous solution phase techniques allowing the assembly of a peptide in a single series of steps within a relatively short period of time.

SUMMARY OF THE INVENTION

A new process has now been found for rapid continuous solution synthesis of peptides, wherein a scavenger is used which allows an essentially arbitrary choice of the amino-protecting group (the protecting group at the N-terminus of the activated carboxylic component). In contrast to the Carpino process, deprotection of the N-terminal function does not necessarily take place under the same reaction conditions as the scavenging of excess of activated carboxylic functions. Therefore, the process of this invention is much more generally applicable than the Carpino process.

The new process according to this invention is a process for rapid solution synthesis of a peptide in an organic solvent or a mixture of organic solvents comprising repetitive cycles of steps (a)-(d):

DETAILED DESCRIPTION (a) a coupling step, using an excess of an activated carboxylic component to acylate an amino component, (b) a quenching step in which a scavenger is used to remove residual activated carboxylic functions, wherein the scavenger may also be used for deprotection of the growing peptide (i.e. the peptide that is being formed), (c) one or more aqueous extractions and optionally, (d) a separate deprotection step, possibly followed by one or more aqueous extractions, characterised in that the process comprises at least one step (b), referred to as step (b'), in which an amine comprising a free anion or a latent anion is used as a scavenger of residual activated carboxylic functions.

During the process of this invention the growing peptide need not be isolated until the final peptide sequence (i.e. final product of the process of this invention) has been obtained. Therefore, the process is significantly less time-consuming than the classical solution phase processes and easy to scale up. The process of this invention allows for highly efficient removal of residual activated carboxylic component without encountering the hydrophobicity problems of other prior art processes in which polyamines are used as scavengers. Thus peptides of high purity are obtained.

Preferably, in step (a) of the process of this invention the molar amounts of the reagents used are in decreasing order:

carboxylic component, coupling additive>coupling reagent>amino component. Further preferred is a process wherein in step (a) a pre-activated carboxylic component is used.

In another preferred embodiment, in step (b') an amine comprising a latent anion is used as the scavenger. Preferably, the latent anion in the scavenging amine bears a temporary protecting group which can be selectively removed in the presence of any permanent protecting group attached to the growing peptide. In a particularly preferred embodiment the protecting group of the latent anion in the scavenging amine displays a lability similar to that of the temporary protecting group present at the N-terminus of the growing peptide. This allows the deprotection of the scavenger yielding the anion and the N-terminal deprotection of the growing peptide to take place in a single process step. Especially preferred is the process of the invention wherein the temporary protecting groups, present at the N-terminus of the growing peptide and optionally present in the scavenger, are hydrogenolytically removable groups whereas the permanent protecting groups are acidolytically removable protecting groups. Preferably, said temporary protecting groups are of the benzyl type, e.g. (substituted) benzyl and benzyloxycarbonyl groups. A preferred scavenger is a primary amine comprising a free anion or a latent anion, and in particular a C-terminally protected amino acid derivative. Besides carboxylate, the scavenging amine may comprise other anionic functions such as—but not limited to—sulfonate, sulfate, phosphonate, phosphate or phenolate. A highly preferred amino acid for use as a scavenger is β3-alanine or a derivative thereof (e.g. an ester or sily ester derivative). The most preferred scavenger is benzyl β-alaninate or a salt thereof.

A thiol comprising a free or a latent anion may also be used as a scavenger instead of an amine comprising a free or a latent anion according to the process of this invention.

The scavenger is preferably used in a two- to sixfold molar excess with respect to the residual active component that needs to be scavenged.

The use of a scavenger according to the present invention leads to hydrophilic scavenged compounds which may be actively extracted into a basic aqueous phase after the deprotection step: upon deprotection (if applicable), hydrophilicity is enhanced by the presence of both a free amino function and a free carboxylic function in the scavenged species. Thus, the process of this invention results in a very effective intermittent purification due to the possibility of actively extracting a hydrophilic scavenged compound. In addition, a possibly present excess of carboxylic component which was not activated and whose temporary protecting group was also removed during deprotection, is extracted from the reaction mixture at the same time.

According to the process of this invention, at least one cycle, but possibly more cycles of the process comprise(s) a step (b') wherein a free anion or a latent anion is used as a scavenger of residual activated carboxylic functions. However, according to a further embodiment of this invention, the process may comprise also one or more cycles wherein in step (b) a polyamine, such as 3-dimethylamino-1-propylamine, is used as the scavenger.

Another preferred process of this invention comprises one or more cycles wherein in step (b) deprotection does not occur (thus the circumstances are chosen such that the scavenger is only used for quenching, e.g. using the Z protecting group and an amine comprising a latent anion as a scavenger) and the subsequent step (c) comprises sequential basic, acidic and basic extractions, which are preferably performed in the presence of sodium chloride or potassium nitrate. This process comprises a subsequent step (d) which comprises deprotection and sequential basic and neutral extractions; these extractions are preferably performed in the presence of sodium chloride or potassium nitrate.

Another preferred process of this invention comprises one or more cycles wherein in step (b) both quenching and deprotection occur (e.g. using the Bsmoc protecting group and a polyamine as a scavenger) and the subsequent step (c) comprises sequential basic and neutral extractions, which are preferably performed in the presence of sodium chloride or potassium nitrate.

Also preferred is a process, wherein in the last cycle in step (a) the protecting groups of the carboxylic component display a similar lability to that of the permanent protecting groups of the amino component and in step (b) the scavenger is a polyamine.

The process according to this invention may be performed in several organic solvents which are commonly used for the production of peptides. A highly preferred organic solvent is ethyl acetate. Also preferred are mixtures of ethyl acetate and other organic solvents, such as dichloromethane, 1-methyl-2-pyrrolidinone, N,N-dimethylformamide or tetrahydrofuran.

The process of this invention may be performed at temperatures well known in the art for such steps in classical solution phase peptide synthesis. However, preferably the process is performed within a temperature range of 0 to 50° C., and in particular at ambient temperature.

The process of this invention is very suitable for combinatorial synthesis of peptide libraries using the split and mix method. Couplings are performed separately while the individual coupling mixtures are combined for extractions and deprotections.

The process of this invention is very suitable for automation since standard protocols are used. The new process of this invention is a highly efficient process which may conveniently be used in the production of oligo- and polypeptides of high purity.

A suitable process according to the present invention is the coupling of an excess of a carboxylic component to an amino component, wherein the carboxylic function is pre-activated or activated in situ using a coupling reagent and, if desired, an additive. Following the coupling step, residual activated carboxylic functions are scavenged by adding the scavenger to the reaction mixture and mixing, usually followed by aqueous extraction. Subsequently or during scavenging, temporary protecting groups are removed using suitable methods known in the art, usually followed by removal of the scavenged compound by aqueous extraction. At the same time, a possibly present excess of carboxylic component which was not activated and whose temporary protecting group was also removed during deprotection, as well as other water-soluble reagents and by-products are extracted from the reaction mixture. Next, another cycle of coupling, quenching, deprotection and extraction steps may follow depending on the length of the desired peptide.

The term amino component refers to a molecule comprising a free amino function. In particular, the amino component may be any amine, amino acid or oligopeptide which bears a free amino function and whose other functional groups are protected in such a manner that they do not interfere with the desired coupling reaction. The C-terminal function of the applied amino acid or oligopeptide may be protected as a substituted or unsubstituted amide or as an ester; examples of the latter include —but are not limited to —methyl, ethyl, t-butyl, benzyl, phenacyl, 3-(3-methyl)pentyl (Mpe), 2-(2-phenyl)propyl (Pp), 2-chlorotrityl (Clt), diphenyl(4-pyridyl)

methyl (PyBzh), dicyclopylmethyl (Dcpm), 9-fluorenylmethyl (Fm), allyl (All), 2-(trimethylsilyl)ethyl (Tmse), 4-{N-[1-(4,4-dimethyl-2,6-dioxocyclohexylidene)-3-methylbutyl]-amino}benzyl (Dmab) esters and enzymatically cleavable esters [Roeske, R. W. (1981) in: '*The Peptides*', vol. 3 (Gross, E. and Meienhofer, J., eds.) Academic Press, New York, pp. 101-136; for Mpe: Karlström, A. and Undén, A. (1996) *Tetrahedron Lett.* 37, 4343-4246; for Pp: Yue, C. et al. (1993) *Tetrahedron Lett.* 34, 323-326; for Clt: Athanassopoulos, P. et al. (1995) *Tetrahedron Lett.* 36, 5645-5648; for PyBzh: Mergler, M. et al. (2001) P154, $2^{nd}$ International Peptide Symposium & $17^{th}$ American Peptide Symposium; for Dcpm: Carpino, L. A. et al. (1995) *J. Org. Chem.* 60, 7718-7719; for Fm: Al-Obeidi, F. et al. (1990) *Int. J. Peptide Protein Res.* 35, 215-218; for All: Kunz, H. et al. (1985) *Int. J. Peptide Protein Res.* 26, 493-497; for Tmse: Sieber, P. (1977) *Helv. Chim. Acta* 60, 2711-2716; for Dmab: Chan, W. C. et al. (1995) *J. Chem. Soc., Chem. Commun.*, 2209-2210]. Functions of the t-butyl type or functions of similar lability are preferred for the permanent protection of other functional groups in the amino component; these include—but are not limited to—t-butyl ($^t$Bu) for the protection of the Asp, Glu, Ser, Thr and Tyr side chains, t-butoxycarbonyl (Boc) for the protection of the Lys and Trp side chains, trityl (Trt) for the protection of the Asn, Gln and His side chains and 2,2,5,7,8-pentamethylchromane-6-sulfonyl (Pmc) or 2,2,4,6,7-pentamethyldihydrobenzofurane-5-sulfonyl (Pbf) for the protection of the Arg side chain [Barany, G. and Merrifield, R. B. (1980) in: '*The Peptides*', vol. 2 (Gross, E. and Meienhofer, J., eds.) Academic Press, New York, pp. 1-284; for Trp(Boc): Franzén, H. et al. (1984) *J. Chem. Soc., Chem. Commun.*, 1699-1700; for Asn(Trt) and Gln(Trt): Sieber, P. and Riniker, B. (1991) *Tetrahedron Lett.* 32, 739-742; for His(Trt): Sieber, P. and Riniker, B. (1987) *Tetrahedron Lett.* 28, 6031-6034; for Pmc: Ramage, R. and Green, J. (1987) *Tetrahedron Lett.* 28, 2287-2290; for Pbf: Carpino, L. A. et al. (1993) *Tetrahedron Lett.* 34, 7829-7832].

The term carboxylic component refers to a molecule comprising a free carboxylic function. In particular, the carboxylic component may be any carboxylic acid, amino acid or oligopeptide which bears a free carboxylic function and whose other functional groups are protected in such a manner that they do not interfere with the desired coupling reaction. In a preferred embodiment, the amino group of the applied amino acid or oligopeptide is temporarily protected by a benzyloxycarbonyl (Z) function; other examples include—but are not limited to—the Boc, Trt, fluoren-9-ylmethoxycarbonyl (Fmoc), 2-(methylsulfonyl)ethoxycarbonyl (Msc), allyloxycarbonyl (Alloc) functions, functions of the arylsulfonyl type, such as ortho-nitrobenzenesulfonyl (o-NBS) and enzymatically cleavable functions [Geiger, R. and König, W. (1981) in: '*The Peptides*', vol. 3 (Gross, E. and Meienhofer, J., eds.) Academic Press, New York, pp. 1-99; for Alloc: Kunz, H. and Unverzagt, C. (1984) *Angew. Chem.* 96, 426-427; for arylsulfonyl: Fukuyama, T. et al. (1997) *Tetrahedron Lett.* 38, 5831-5834]. Functions of the t-butyl type or functions of similar lability are preferred for the permanent protection of other functional groups in the carboxylic component, as described above for the amino component. The carboxylic component may be preactivated as an active ester, preferably an N-hydroxysuccinimide, benzotriazol-1-yl, pentafluorophenyl or 4-nitrophenyl ester, a halide, an N-carboxyanhydride or as a symmetric anhydride. Alternatively, the carboxylic component may be activated in situ as a mixed anhydride or using a coupling reagent, such as a carbodiimide, preferably N,N'-dicyclohexylcarbodiimide (DCC) or 1-(3'-dimethylaminopropyl)-3-ethylcarbodiimide hydrochloride (EDC), a uronium or a phosphonium salt in the possible presence of a coupling additive, preferably N-hydroxysuccinimide (HONSu), 1-hydroxybenzotriazole (HOBt), 3-hydroxy-4-oxo-3,4-dihydro-1,2,3-benzotriazine (HOOBt), 1-hydroxy-7-azabenzotriazole (HOAt) or 6-chloro-1-hydroxybenzotriazole (Cl-HOBt) and if required in the presence of a tertiary amine ['*The Peptides*', vol. 1 (1979) (Gross, E. and Meienhofer, J., eds.) Academic Press, New York; Li, P. and Xu, J.-C. (2000) *Chin. J. Chem.* 18, 456-466].

The temporary protecting group may be removed according to methods known in the art (vide supra). The Z function may be removed by hydrogenolysis using (standard) procedures that apply, e.g. hydrogen gas or formiate as a hydrogen donor. During this proces all benzyl-type protecting groups are removed and protecting groups of the t-butyl type or functions of similar lability are maintained. The latter may be removed by acidolysis according to the methods known in the art.

A person skilled in the art will understand what is meant with the term basic aqueous extraction. However, basic aqueous extractions are preferably performed using aqueous solutions of sodium hydrogencarbonate or sodium carbonate, if desired in the presence of sodium chloride or potassium nitrate. The term active aqueous extraction refers to an extraction in which either an amino component is extracted under acidic conditions in the protonated form (ammonium) or a carboxylic component is extracted under basic conditions in the deprotonated form (carboxylate).

The invention is further illustrated by the following examples, which are not to be interpreted as a limitation of this invention.

EXAMPLE 1

Boc-Gly-Phe-Asp(O$^t$Bu)-Ser($^t$Bu)-O$^t$Bu $1^{st}$ Cycle: To a stirred solution of 4.34 g of H-Ser($^t$Bu)-O$^t$Bu in a mixture of ethyl acetate and dichloromethane at 20° C., were added 3.24 g of 1-hydroxybenzotriazole, 7.76 g of Z-Asp(O$^t$Bu)-OH, 4.20 g of 1-(3'-dimethylaminopropyl)-3-ethylcarbodiimide hydrochloride and 2.42 ml of 4-methylmorpholine. After stirring the resulting solution until completion of the reaction, 1.21 ml of 4-methylmorpholine and 3.51 g of benzyl β-alaninate p-toluenesulfonate salt were added. The mixture was stirred for another 30 minutes and was extracted with 5% $Na_2CO_3$/10% NaCl, 5% $KHSO_4$/10% NaCl and 5% $Na_2CO_3$/10% NaCl.

The organic layer containing the protected dipeptide Z-Asp(O$^t$Bu)-Ser($^t$Bu)-O$^t$Bu was subjected to catalytic hydrogenolysis in the presence of palladium on charcoal. Upon completion of the reaction, 5% $Na_2CO_3$/10% NaCl was added and the resulting suspension was filtered. The residue was washed with a mixture of ethyl acetate and dichloromethane, and the combined organic filtrates were extracted with 5% $Na_2CO_3$/10% NaCl and 30% NaCl.

$2^{nd}$ Cycle: To the organic layer containing the dipeptide H-Asp(O$^t$Bu)-Ser($^t$Bu)-O$^t$Bu at 20° C., were added 3.24 g of 1-hydroxybenzotriazole, 7.18 g of Z-Phe-OH, 4.20 g of 1-(3'-dimethylaminopropyl)-3-ethylcarbodiimide hydrochloride and 2.42 ml of 4-methylmorpholine.

After stirring the resulting solution until completion of the reaction, 1.21 ml of 4-methylmorpholine and 3.51 g of benzyl β-alaninate p-toluenesulfonate salt were added. The mixture was stirred for another 30 minutes and was extracted with 5% $Na_2CO_3$/10% NaCl, 5% $KHSO_4$/10% NaCl and 5% $Na_2CO_3$/10% NaCl.

The organic layer containing the protected tripeptide Z-Phe-Asp(O$^t$Bu)-Ser($^t$Bu)-O$^t$Bu was subjected to catalytic hydrogenolysis in the presence of palladium on charcoal. Upon completion of the reaction, 5% Na$_2$CO$_3$/10% NaCl was added and the resulting suspension was filtered. The residue was washed with a mixture of ethyl acetate and dichloromethane, and the combined organic filtrates were extracted with 5% Na$_2$CO$_3$/10% NaCl and 30% NaCl.

3$^{rd}$ Cycle: To the organic layer containing the tripeptide H-Phe-Asp(O$^t$Bu)-Ser($^t$Bu)-O$^t$Bu at 20° C., were added 3.24 g of 1-hydroxybenzotriazole, 4.21 g of Boc-Gly-OH, 4.20 g of 1-(3'-dimethylaminopropyl)-3-ethylcarbodiimide hydrochloride and 2.42 ml of 4-methylmorpholine. After stirring the resulting solution until completion of the reaction, 1.25 ml of 3-dimethylamino-1-propylamine was added. The mixture was stirred for another 30 minutes and was extracted with 5% Na$_2$CO$_3$/10% NaCl, 5% KHSO$_4$/10% NaCl, 5% Na$_2$CO$_3$/10% NaCl, 30% NaCl and water. The organic layer was evaporated to dryness and the residue triturated with methyl tert-butyl ether and dried to give the desired protected tetrapeptide in 95% yield based on the starting material H-Ser($^t$Bu)-O$^t$Bu. The process was completed within 6 hours.

Purity: 98.1% by reversed phase HPLC (24 to 68% acetonitrile in 0.1% trifluoroacetic acid in 29 minutes at 220 nm, 2.0 ml/min, 5 micron C$_{18}$ column). Identity: m/z 425.4 [M-Boc-3$^t$Bu+H]$^+$, 469.4 [M-4$^t$Bu+H]$^+$, 525.4 [M-3$^t$Bu+H]$^+$, 581.4 [M-2$^t$Bu+H]$^+$, 637.4 [M-$^t$Bu+H]$^+$, 693.4 [M+H]$^+$ by electrospray MS; $^1$H NMR (CDCl$_3$) δ 1.16 (s, 9H), 1.44 (m, 27H), 2.59 (dd, 1H), 2.79 (dd, 1H), 3.09 (m, 2H), 3.51 (dd, 1H), 3.69-3.86 (m, 3H), 4.47 (m, 1H), 4.67-4.78 (m, 2H), 5.20 (bs, 1H), 6.68 (d, 1H), 7.12-7.34 (m, 7H).

EXAMPLE 2

H-His-Trp-Ser($^t$Bu)-Tyr($^t$Bu)-D-Leu-Leu-Orn(Boc)-Pro-O$^t$Bu

1$^{st}$ Cycle: To a stirred solution of 1300 g of H-Pro-O$^t$Bu.HCl in ethyl acetate at 20° C., were added 1014 g of 1-hydroxybenzotriazole, 2756 g of Z-Orn(Boc)-OH, 1378 g of 1-(3'-dimethylaminopropyl)-3-ethylcarbodiimide hydrochloride and 1495 ml of 4-methylmorpholine.

After stirring the resulting solution until completion of the reaction, 377 ml of 4-methylmorpholine and 1105 g of benzyl β-alaninate p-toluenesulfonate salt were added. The mixture was stirred for another 30 minutes and was extracted with 5% Na$_2$CO$_3$/10% NaCl, 5% KHSO$_4$/10% NaCl and 5% Na$_2$CO$_3$/10% NaCl.

The organic layer containing the protected dipeptide Z-Orn(Boc)-Pro-O$^t$Bu was subjected to catalytic hydrogenolysis in the presence of palladium on charcoal. Upon completion of the reaction, 5% Na$_2$CO$_3$/15% NaCl was added and the resulting suspension was filtered. The residue was washed with ethyl acetate, and the combined organic filtrates were extracted with 5% Na$_2$CO$_3$/15% NaCl and 30% NaCl. The separate aqueous layers were re-extracted with ethyl acetate.

2$^{nd}$ Cycle: To the combined organic layers containing the dipeptide H-Orn(Boc)-Pro-O$^t$Bu at 20° C., were added 1014 g of 1-hydroxybenzotriazole, 1993 g of Z-Leu-OH, 1320 g of 1-(3'-dimethylaminopropyl)-3-ethylcarbodiimide hydrochloride and 754 ml of 4-methylmorpholine. After stirring the resulting solution until completion of the reaction, 377 ml of 4-methylmorpholine and 1105 g of benzyl β-alaninate p-toluenesulfonate salt were added. The mixture was stirred for another 30 minutes and was extracted with 5% Na$_2$CO$_3$/10% NaCl, 5% KHSO$_4$/10% NaCl and 5% Na$_2$CO$_3$/10% NaCl.

The organic layer containing the protected tripeptide Z-Leu-Orn(Boc)-Pro-O$^t$Bu was subjected to catalytic hydrogenolysis in the presence of palladium on charcoal. Upon completion of the reaction, 5% Na$_2$CO$_3$/15% NaCl was added and the resulting suspension was filtered. The residue was washed with ethyl acetate, and the combined organic filtrates were extracted with 5% Na$_2$CO$_3$/10% NaCl and 30% NaCl.

3$^{rd}$ Cycle: To the organic layer containing the tripeptide H-Leu-Orn(Boc)-Pro-O$^t$Bu at 20° C., were added 1014 g of 1-hydroxybenzotriazole, 1993 g of Z-D-Leu-OH, 1320 g of 1-(3'-dimethylaminopropyl)-3-ethylcarbodiimide hydrochloride and 754 ml of 4-methylmorpholine. After stirring the resulting solution until completion of the reaction, 377 ml of 4-methylmorpholine and 1105 g of benzyl β-alaninate p-toluenesulfonate salt were added. The mixture was stirred for another 30 minutes and was extracted with 5% Na$_2$CO$_3$, 5% KHSO$_4$ and 5% Na$_2$CO$_3$.

The organic layer containing the protected tripeptide Z-D-Leu-Leu-Orn(Boc)-Pro-O$^t$Bu was subjected to catalytic hydrogenolysis in the presence of palladium on charcoal. Upon completion of the reaction, 5% Na$_2$CO$_3$ was added and the resulting suspension was filtered.

The residue was washed with ethyl acetate, and the combined organic filtrates were extracted with 5% Na$_2$CO$_3$ and 10% NaCl.

4$^{th}$ to 7$^{th}$ Cycle: These cycles were performed following the procedure of the third cycle, replacing 1993 g of Z-D-Leu-OH by Z-Tyr($^t$Bu)-OH (liberated from 4497 g of the corresponding dicyclohexylammonium salt), 2218 g of Z-Ser($^t$Bu)-OH, 2538 g of Z-Trp-OH and 2172 g of Z-His-OH, respectively. However, from the fifth cycle onwards the amounts of 4-methylmorpholine and benzyl β-alaninate p-toluenesulfonate salt during the scavenging step were doubled. In the fifth cycle, the extractions following scavenging were performed at 35° C. In the seventh cycle, coupling was performed at 3° C., 1014 g of 1-hydroxybenzotriazole was replaced by 2561 g of 6-chloro-1-hydroxybenzotriazole and a supplementary portion of 132 g of 1-(3'-dimethylaminopropyl)-3-ethylcarbodiimide hydrochloride was added after 1 hour coupling. Also in the seventh cycle, the extractions following hydrogenolysis were performed at 35° C. At the end of the seventh cycle, the organic layer was evaporated to dryness to give the desired protected nonapeptide in 73% yield based on the starting material H-Pro-O$^t$Bu.HCl (i.e., on average 98% per chemical step).

Purity: 90.6% by reversed phase HPLC (24 to 68% acetonitrile in 0.1% trifluoroacetic acid in 29 minutes at 220 nm, 2.0 ml/min, 5 micron C$_{18}$ column). Identity: m/z 543.6 [M-Boc-2$^t$Bu+2H]$^{2+}$, 571.6 [M-Boc-$^t$Bu+2H]$^{2+}$, 599.6 [M-Boc+2H]$^{2+}$, 649.8 [M+2H]$^{2+}$, 1298.0 [M+H]$^+$ by electrospray MS.

Conclusions: The protected peptides were produced without intermittent isolation of the intermediates. The purity and identification of the obtained product from the first example demonstrate that the excesses of (activated) carboxylic components have been removed completely in all stages of the processes and no insertion sequences have been formed using the process of this invention. The synthesis from the second example, moreover, demonstrates that synthesis according to the process of this invention is easily upscalable. The products from both examples are obtained in high yield and high purity within a relatively short period of time.

The invention claimed is:

1. A process for solution synthesis of a peptide in an organic solvent or a mixture of organic solvents, the process comprising repetitive cycles of steps (a)-(c):
   wherein step (a) comprises a coupling step, using an excess of a molecule comprising an activated carboxylic component comprising at least one temporary protecting group to acylate an amino component,
   wherein step (b) comprises a quenching step in which a scavenger is used to remove residual activated carboxylic functions, wherein the scavenger may also be used for deprotection of the at least one temporary protecting group on the growing peptide;
   wherein step (c) comprises one or more aqueous extractions,
   and wherein the process comprises at least one step (b), referred to as step (b'), in which an amine comprising a free anion or a latent anion is used as a scavenger of residual activated carboxylic functions, and wherein the anion is selected from the group consisting of carboxylate, sulfonate, sulfate, phosphonate, phosphate and phenolate.

2. The process of claim 1, wherein in step (a) the molecule comprising an activated carboxylic component is formed by reacting a carboxylic component, a coupling additive and a coupling reagent and wherein the molar amounts of the reagents used are in decreasing order:
   carboxylic component, coupling additve>coupling reagent>amino component.

3. The process of claim 1, wherein in step (a) a pre-activated carboxylic component is used.

4. The process of claim 1, wherein in step (b') an amine comprising a latent anion is used as the scavenger.

5. The process of claim 4, wherein the latent anion in the scavenging amine bears a temporary protecting group which can be selectively removed in the presence of any permanent protecting groups attached to the growing peptide.

6. The process of claim 4, wherein the latent anion in the scavenging amine bears a temporary protecting group which displays a lability similar to that of the temporary protecting group present at the N-terminus of the growing peptide.

7. The process of claim 5, wherein the temporary protecting group located on the scavenging amine is a hydrogenolytically removable groups.

8. The process of claim 7, wherein the temporary protecting groups located on the scavenging amine is of the benzyl type.

9. The process of claim 4, wherein the scavenger is a primary amine comprising a free anion or a latent anion.

10. The process of claim 9, wherein the primary amine is a C-terminally protected amino acid derivative.

11. The process of claim 10, wherein the amino acid is β-alanine or a derivative thereof.

12. The process of claim 11, wherein the scavenger is benzyl β-alaninate or a salt thereof.

13. The process of claim 1, comprising one or more cycles wherein in step (b) a polyamine is used as the scavenger.

14. The process of claim 1, comprising one or more cycles wherein in step (b) both quenching and deprotection occur and the subsequent step (c) comprises sequential basic and neutral extractions.

15. The process of claim 14, wherein the extractions are performed in the presence of sodium chloride or potassium nitrate.

16. The process of claim 1, wherein in the last cycle in step (a) the at least one temporary protecting groups of the carboxylic component displays a similar lability to that of at least one permanent protecting group that is also attached to the growing peptide and in step (b) the scavenger is a polyamine.

17. The process of claim 1, wherein the organic solvent or mixture of organic solvents is ethyl acetate or a mixture of ethyl acetate and dichloromethane, a mixture of ethyl acetate and 1-methyl-2-pyrrolidinone, a mixture of ethyl acetate and N,N-dimethylformamide or a mixture of ethyl acetate and tetrahydrofuran.

18. The process of claim 1, wherein the process is performed within a temperature range of 0 to 50° C.

19. The process of claim 18, wherein the process is performed at ambient temperature.

20. The process of claim 1, the process applied in a method for automated solution synthesis of peptides.

21. The process of claim 5, wherein the permanent protecting groups are acidolytically removable groups.

22. The process of claim 1, wherein a thiol comprising a free or a latent anion is used as a scavenger instead of an amine comprising a free or a latent anion.

23. The process of claim 1, comprising one or more cycles wherein in step (b) deprotection does not occur and the subsequent step (c) comprises sequential basic, acidic and basic extractions.

24. The process of claim 23, wherein the extractions are performed in the presence of sodium chloride or potassium nitrate.

25. The process of claim 23, comprising a subsequent step (d) which comprises deprotection and sequential basic and neutral extractions.

26. The process of claim 25, wherein the extractions are performed in the presence of sodium chloride or potassium nitrate.

27. The process of claim 1, wherein the process further comprises at least one step (d), wherein step (d) comprises a separate deprotection step, followed by one or more aqueous extractions.

28. The process of claim 1, wherein the anion is carboxylate.

29. The process of claim 1, wherein the anion is sulfonate.

30. The process of claim 1, wherein the anion is sulfate.

31. The process of claim 1, wherein the anion is phosphonate.

32. The process of claim 1, wherein the anion is phosphate.

33. The process of claim 1, wherein the anion is phenolate.

34. The process of claim 1, wherein the anion is formed under basic aqueous conditions.

35. A method for combinatorial synthesis of a peptide library, wherein the process of claim 1 is used in a split and mix fashion to produce a peptide library.

36. The process of claim 6, wherein the temporary protecting group located on the scavenging amine is a hydrogenolytically removable group.

37. The process of claim 36, wherein the temporary protecting group located on the scavenging amine is of the benzyl type.

* * * * *